United States Patent
Donitzky et al.

(10) Patent No.: US 10,828,506 B2
(45) Date of Patent: Nov. 10, 2020

(54) CROSSLINKING CONTROL

(71) Applicant: Wavelight GmbH, Erlangen (DE)

(72) Inventors: Christof Donitzky, Eckental (DE);
Armin Wellhoefer, Schwaig (DE)

(73) Assignee: Alcon Inc. (CH)

( * ) Notice: Subject to any disclaimer, the term of this patent is extended or adjusted under 35 U.S.C. 154(b) by 406 days.

(21) Appl. No.: 15/024,827

(22) PCT Filed: Oct. 30, 2013

(86) PCT No.: PCT/EP2013/072710
§ 371 (c)(1),
(2) Date: Mar. 24, 2016

(87) PCT Pub. No.: WO2015/062648
PCT Pub. Date: May 7, 2015

(65) Prior Publication Data
US 2016/0236006 A1    Aug. 18, 2016

(51) Int. Cl.
*A61F 9/008* (2006.01)
*A61N 5/06* (2006.01)
*A61F 9/007* (2006.01)

(52) U.S. Cl.
CPC .............. *A61N 5/062* (2013.01); *A61F 9/008* (2013.01); *A61F 9/0079* (2013.01); *A61F 2009/00851* (2013.01); *A61F 2009/00872* (2013.01)

(58) Field of Classification Search
CPC .................................. A61F 9/008; A61N 5/06
See application file for complete search history.

(56) References Cited

U.S. PATENT DOCUMENTS

| | | | |
|---|---|---|---|
| 2008/0208177 A1* | 8/2008 | Mrochen | A61F 9/008 606/5 |
| 2009/0149842 A1* | 6/2009 | Muller | A61B 18/18 606/5 |
| 2011/0301524 A1 | 12/2011 | Bueler et al. | |
| 2013/0060187 A1* | 3/2013 | Friedman | A61F 9/0008 604/20 |

FOREIGN PATENT DOCUMENTS

WO    2013/059837 A2    4/2013

\* cited by examiner

*Primary Examiner* — Lynsey C Eiseman

(57) ABSTRACT

A crosslinking control system, the use of the crosslinking control system, a laser system comprising the crosslinking control system, a crosslinking control method and a method for laser treatment are provided. The crosslinking control system comprises a photosensitizer providing unit, a light source configured to provide light having a wavelength suitable to activate the photosensitizer introduced into or applied onto the tissue for crosslinking, and a control computer.

18 Claims, 8 Drawing Sheets

CROSSLINKING CONTROL

CROSS REFERENCE TO RELATED APPLICATIONS

Figure 1:
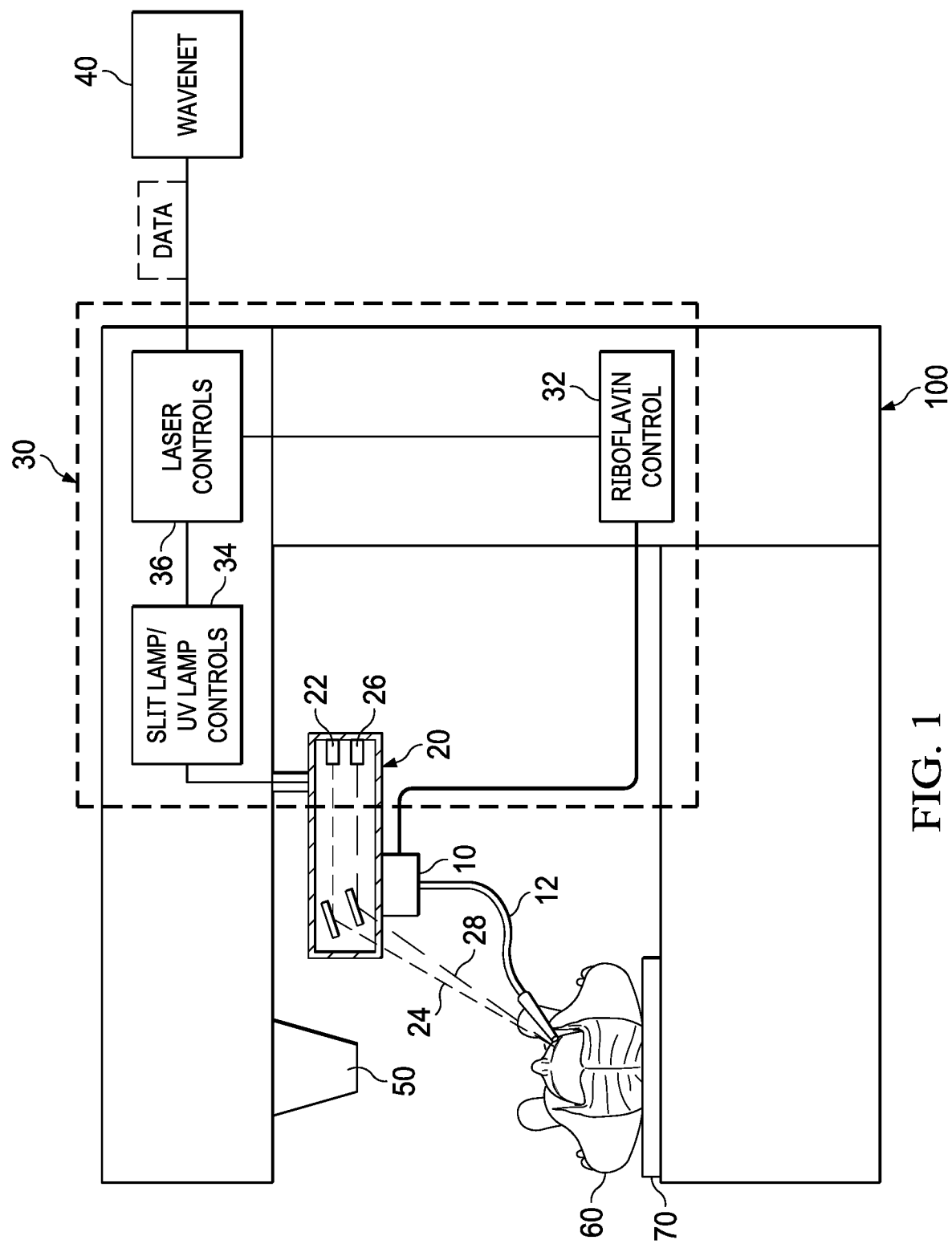

This application claims priority to International Application Serial Number PCT/EP2013/072710, filed 30 Oct. 2013, titled "CROSSLINKING CONTROL," which is hereby incorporated by reference in its entirety.

TECHNICAL FIELD

The present disclosure generally relates to crosslinking of tissue. More particularly, embodiments of the present disclosure relate to a crosslinking control system, the use of the crosslinking control system, a laser system comprising the crosslinking control system, a crosslinking control method and a method for laser treatment.

BACKGROUND

In ophthalmology, the technique of using a photosensitizer and electromagnetic radiation to change the biomechanical and biochemical properties of tissue, e.g., the cornea, for therapeutic purposes has been known for more than 10 years.

The human eyeball is bounded by the corneosclera. Due to internal eye pressure, the corneosclera, which contains collagen, has an approximately spherical shape. In the posterior eyeball region, the corneosclera consists of white sclera. The cornea, which is translucent to visible light, is situated in the anterior region.

Deformations of the corneosclera can cause ametropia. For example, axial myopia, a type of myopia, can result from a cornea and/or sclera longitudinal expansion of the eyeball. An ellipsoidal shaped corneal surface can cause a form of astigmatism or other high order aberration, which is called "irregular corneal curvature". In the laser treatment of an eye to correct ametropia, e.g., using an excimer or femtosecond laser, under certain circumstances (for example, in the case of unstable tissue or an overly thin cornea) it is necessary to stabilize the tissue of the eye before the treatment, to guarantee safe treatment.

Another defect of the cornea can be caused by progressive and irregular changes in corneal shape. This is typically known as ectasia. These ectatic changes are typically marked by corneal thinning and an increase in the anterior and/or posterior curvatures of the cornea, and often lead to high levels of myopia and astigmatism. The most common form of ectasia is keratoconus. Keratoconus, a pathological softening of the cornea, leads to a progressive thinning and cone-shaped deformation of the cornea. As the bulging increases, the cornea becomes typically thinner below the center. It can fracture and become scarred, which can permanently reduce visual acuity. In these conditions, the corneal stroma is structurally weakened and biomechanically unstable.

During corneal surgery there may be destabilization of the corneal integrity due to photodisruption or photoablation of corneal tissue as well as through mechanical incisions by metal or diamond knifes.

Corneal crosslinking (which is also often referred to as corneal cross-linking, corneal collagen crosslinking or corneal collagen cross-linking) is a technique which uses ultraviolet (UV) light or light in the blue spectrum and a photosensitizer to strengthen chemical bonds in the cornea and to thereby increase the corneal stiffness. The stiffening effect results from UV radiation of the photosensitizer. By means of the UV radiation, the photosensitizer is activated to cause corneal crosslinking. Corneal crosslinking involves the cross-linking of collagen fibers.

In short, corneal crosslinking may be regarded as the process of placing a photosensitizer onto or into the cornea followed by exposure to UV light, in order to stiffen the cornea. Crosslinking is generally not limited to applications on or in eye tissue. Rather applications with all kinds of tissue are conceivable, which will herein generally be referred to as crosslinking.

For example, corneal crosslinking has been used extensively for stabilizing keratoconic corneas to prevent further progression of this disease.

In known techniques, the corneal epithelium is at least partially removed to introduce riboflavin as one example of a photosensitizer into the cornea, because the epithelium hinders the riboflavin from penetrating the cornea by acting as a barrier to the diffusion of the riboflavin molecules into the cornea. More recently, it has been proposed to create channels in the cornea by means of a laser device, to introduce riboflavin into the created channels and to irradiate the introduced riboflavin by means of a suitable additional UV light source. During UV irradiation of riboflavin intrastomally a production of singlet oxygen radicals introduces collagen crosslinking between collagen fibrils based on the formation of covalent and trivanent crosslinks. The UV irradiation requires that either the additional UV light source is moved to the patient or the patient is moved to the additional UV light source.

In such known techniques, the treatment steps are performed manually, so that, for example, a certain waiting time exists for the patient and the treating physician(s). The waiting time results from a manual diagnosis of the patient, the resulting time-delayed and manual introduction or application of the photosensitizer and strengthening thereof, and again the time-delayed refractive treatment with the UV light.

SUMMARY

There is a need to provide an improved technique for crosslinking, e.g., for corneal crosslinking.

According to a first aspect, a crosslinking control system is provided. The crosslinking control system comprises: a photosensitizer providing unit, a light source, and a control computer. The photosensitizer providing unit is configured to provide photosensitizer for introduction or application of the photosensitizer into or onto tissue. The light source is configured to provide light having a wavelength suitable to activate the photosensitizer introduced into or applied onto the tissue for crosslinking. The control computer is programmed to determine one or more control parameters for control of at least one of the activation of the photosensitizer and the introduction or application of the photosensitizer.

A control program may be provided in and executable on the control computer. The control program may contain instructions that, when executed by the control computer, execute control operations as described herein. In this way, the control computer may be programmed to control at least one of the activation of the photosensitizer and the introduction or application of the photosensitizer by considering the determined one or more control parameters.

The tissue may be or comprises eye tissue, e.g., corneal tissue. In this case, the crosslinking may be regarded as corneal crosslinking. However, the tissue is not limited to eye tissue but may be or comprise all kinds of tissue.

For corneal crosslinking, the photosensitizer may comprise any suitable ingredients that stabilize corneal tissue, e.g., riboflavin (vitamin B2), lysyloxidase, transglutaminase, sugar aldehydes, ethylcarbodiimid, glutaraldehyde, formaldehyde or mixtures of these e.g., Karnovsky solution. At least some of the aforementioned photosensitizers may also be used for other tissue than eye tissue like corneal tissue.

It has been found that light in the wavelength range from 190 nm to 500 nm, e.g., 270 nm, 366 nm or 445 nm, is appropriate for activating photosensitizer for corneal crosslinking, which are currently commonly used. For example, current technologies use riboflavin as a photosensitizer and an ultraviolet (UV) light source as the light source. For example, the light source may be configured to provide light in a wavelength range from 360 nm to 370 nm for corneal crosslinking, i.e., to mitigate new intracorneal protein connections. In the wavelength range from 360 nm to 370 nm human cornea soaked with riboflavin is maximally absorbed. However, other photosensitizers may be conceivable in the future, which may be activated by irradiation (which may also be named illumination) with light in wavelength ranges differing from the aforementioned exemplary range(s). By corneal crosslinking, the stress of the cornea may be improved by a factor of up to 1.5.

The one or more control parameters for control of the activation of the photosensitizer comprise at least one of: information specifying the duration of irradiation of the photosensitizer with the light, information specifying the intensity of the light for irradiating the photosensitizer, information specifying the wavelength of the light for irradiating the photosensitizer, information specifying the spatial distribution of the light in or on the tissue, and information specifying the temporal distribution of the light in or on the tissue.

The information specifying the duration of irradiation of the photosensitizer with the light may be or comprise information specifying for how long the photosensitizer is to be continuously or repetitively irradiated. For example, the duration of irradiation may be or comprise one or more time periods. The information specifying the spatial distribution of the light in or on the tissue may be or comprise information specifying one or more locations which are to be irradiated with the light. The information specifying the intensity of the light for irradiating the photosensitizer may be or comprise information about one or more intensity profiles of the light at respective one or more locations on or in the tissue. The intensity profiles may be specified by the mean power of the light at the respective location(s) to be irradiated. For example, if multiple locations are specified for the spatial distribution of the light, the information specifying the intensity may specify different intensities to be achieved at at least a subset of the multiple locations. The information specifying the intensity of the light for irradiating the photosensitizer may comprise information about the maximum dose to be applied to the tissue. For example, in case of the tissue being the cornea of an eye, a maximum dose (energy) of 5 J/cm$^2$ may be applied to the cornea. The information specifying the temporal distribution of the light in or on the tissue may be or comprise information about an interval between subsequent irradiation of the photosensitizer with the light. A desired temporal distribution may be achieved by illuminating parts of the tissue sequentially with the light.

Just to give some exemplary values for some of the control parameters for illustration rather than limitation, the mean power of the light for irradiation (as an example for the intensity of the light) may be in the range of 3 to 100 mW/cm$^2$ or higher, for example, a range of 3-10; 10-30; 30-50; 50-80; 80-100 mW/cm$^2$. The wavelength of the light may lie within a wavelength range from 360 nm to 370 nm. The duration of irradiation may be 30 minutes with an additional application or introduction of photosensitizer every 2 minutes. In case of riboflavin, the additional application or introduction may be necessary because of the conversion of riboflavin into lumiflavin and lumichrome under irradiance of light having a wavelength from 360 nm to 370 nm.

Alternatively or additionally, the one or more control parameters for control of the introduction or application of the photosensitizer comprise at least one of: information specifying the quantity of the photosensitizer to be introduced or applied into or onto the tissue, information specifying one or more positions in or on the tissue for the introduction or application of the photosensitizer, and information specifying one or more points or periods of time for the introduction or application of the photosensitizer.

The information specifying the quantity of the photosensitizer to be introduced or applied into or onto the tissue may be or comprise information specifying one or more dosages to be applied during one or more periods of time. The one or more periods of time may also be specified by the one or more control parameters. The information specifying one or more positions in or on the tissue for the introduction or application of the photosensitizer may specify one or more locations in or on the tissue at which the same or a different amount of photosensitizer can be applied or introduced.

In case of corneal crosslinking, the photosensitizer may be introduced into or applied onto the corneal tissue in a number of different ways.

For example, an epithelial abrasion may be performed first because the epithelium may act as a barrier for the molecules of the photosensitizer.

As another example, at least one incision may be created in the cornea for the introduction or application of the photosensitizer into or onto the cornea as described in U.S. Ser. No. 13/473,004 of the applicant, the content of which is incorporated by reference herein. For sake of completeness, some aspects of creating such at least one incision are briefly summarized. The at least one incision may be or may comprise at least one cut and/or at least one channel incision. The at least one channel incision may be created for the introduction of photosensitizer into the cornea. For example, the at least one channel incision may form one or more channels for the introduction of photosensitizer. The at least one cut may be created for the application of photosensitizer onto the cornea. The at least one incision may be created by means of a laser source configured to provide laser radiation. Examples of laser sources include an attosecond laser, a femtosecond laser, a nanosecond laser, or a picosecond laser. Such laser sources, for example, a femtosecond laser, cut tissue of the eye by photodisruption of the tissue with the energy of the laser light, which creates laser inducted optical breakthrough (LIOB), which generate cavitation bubbles. In LASIK procedure, the laser system cuts a flap or cap in the stroma. The flap/cap is lifted or removed to ablate the exposed stroma using, e.g., an excimer laser in order to reshape the cornea. Pulsed lasers with pulse lengths in the picosecond, nanosecond, femtosecond and attosecond range are suitable for creating the at least one incision, e.g., the at least one cut and/or the at least one channel incision. The laser source may provide laser radiation in a wavelength range of 300-1900 nanometers (nm), for example, a wavelength in the range of 300-650, 650-1050, 1050-1250, or 1100-1900 nm.

The foci of the laser radiation may move along a straight or curved line to yield LIOBs in the tissue in order to produce the at least one incision, e.g., the at least one cut and/or channel incision. The at least one incision may be created such that, on the one hand, the separation of the individual adjacent LIOB from each other (or "spacing" between the bubbles) may impair the structure and stability of the tissue as little as possible. On the other hand, in case at least one channel incision is created, the separation between the LIOBs forming the at least one channel incision may be so small that the photosensitizer, introduced into the at least one channel incision in the form of a solution penetrates into the tissue through the at least one channel incision in the desired manner, i.e., from LIOB to LIOB. In the regions between adjacent LIOBs, the photosensitizer therefore penetrates by diffusion. It follows that in the sense of certain embodiments the term "channel" or "channel incision" is not necessarily to be thought of as a continuous cavity fully free of tissue, although on the other hand completely continuous channels or channel incisions can also be envisaged in certain embodiments. The term "channel" or "channel incision" as used herein in certain embodiments does not mean an incision area for creating a flap/cap as in LASIK. The term "cut" on the other hand, may be understood as a flap/cap, which may then be hardened by crosslinking, e.g., corneal crosslinking.

In summary, the at least one incision, e.g., comprising at least one cut and/or at least one channel incision, may be created by dissecting the cornea by means of the laser radiation provided by the laser source. Then, photosensitizer may be introduced into the at least one channel incision and/or applied onto the at least one cut. The introduced and/or applied photosensitizer may then be activated by irradiating the photosensitizer with the light.

In a first embodiment of the crosslinking control system according to the first aspect, the control computer may be programmed to control the photosensitizer providing unit to provide the photosensitizer for the introduction or application of the photosensitizer in accordance with the determined one or more control parameters. For example, the control computer may be configured to instruct the photosensitizer providing unit to provide the photosensitizer in accordance with at least one of the information specifying the quantity of the photosensitizer to be introduced or applied into or onto the tissue, the information specifying one or more positions in or on the tissue for the introduction or application of the photosensitizer, and the information specifying one or more points or periods of time for the introduction or application of the photosensitizer.

In order to deliver the photosensitizer, the photosensitizer providing unit may further comprise a guiding device configured to guide the photosensitizer into or onto the tissue in accordance with the determined one or more control parameters.

In a second embodiment of the crosslinking control system according to the first aspect, which may be combined with or may be implemented independent from the first embodiment of the crosslinking control system, the control computer may be programmed to control the light source to activate the photosensitizer in accordance with the determined one or more control parameters. For example, the control computer may be configured to instruct the light source to provide the light in accordance with at least one of the information specifying the duration of irradiation of the photosensitizer with the light, the information specifying the intensity of the light for irradiating the photosensitizer, the information specifying the wavelength of the light for irradiating the photosensitizer, the information specifying the spatial distribution of the light in or on the tissue and the information specifying the temporal distribution of the light in or on the tissue.

As stated above, the light source may comprise or may be configured as an UV light source. Alternatively or additionally, the light source may comprise or may be configured as at least one of one or more UV light emitting diodes (LEDs), one or more glass fibers and one or more light waveguides. It is conceivable that a plurality of UV LEDs, glass fibers or light waveguides may be provided as the light source. Each of the plurality of UV LEDs, glass fibers or light waveguides may be configured to alternately deliver light or not in accordance with the instructions of the control computer. In this case, the control computer may select one or more of the plurality of the UV LEDs, glass fibers or light waveguides to provide the light. By selecting one or more of the UV LEDs, glass fibers or light waveguides, one or more partial areas of the tissue may be irradiated with the light. In this way, the crosslinking can be selectively controlled. By alternately changing the selection, the intensity of the light incident on the tissue may be changed.

In a third embodiment of the crosslinking control system according to the first aspect, which may be combined with or may be implemented independent from any of the first and second embodiments of the crosslinking control system, the control system may further comprise a light adjustment apparatus. The control computer may be programmed to control the light adjustment apparatus to adjust the light provided by the light source in accordance with the determined one or more control parameters. For example, the control computer may be configured to instruct the light adjustment apparatus to adjust or change the light provided by the light source in accordance with at least one of the information specifying the duration of irradiation of the photosensitizer with the light, the information specifying the intensity of the light for irradiating the photosensitizer, the information specifying the wavelength of the light for irradiating the photosensitizer, the information specifying the spatial distribution of the light in or on the tissue and the information specifying the temporal distribution of the light in or on the tissue.

For example, the control computer may instruct the light adjustment unit to irradiate only one or more partial areas of the tissue with the light. The light adjustment apparatus may comprise or may be configured as at least one of a diaphragm, a beam delimiter and a digital micromirror device (DMD) which may be suitably controlled by the control computer. In optics, a diaphragm may be regarded as a thin opaque structure with an opening (aperture) at its center. The role of the diaphragm is to stop the passage of light, except for the light passing through the aperture.

Thus it is also called a stop (or an aperture stop). By selectively stopping the light by means of the diaphragm, the intensity of the light may be adjusted, for example. Similarly, a beam delimiter may be used to adjust the light intensity, for example. The DMD may be regarded as an optical semiconductor. A DMD chip may have on its surface several hundred or thousand microscopic mirrors arranged in a rectangular array. The mirrors may be individually rotated, to an on or off state. In the on state, light from the light source is reflected into a lens in order to be irradiated on the tissue. In the off state, the light is directed elsewhere without irradiating the tissue, e.g., into a beam dump. In this way, a desired spatial distribution of the light may be achieved.

The control computer may be configured to repetitively determine at least one of the one or more control parameters. For example, at least one of the one more control parameters may be determined before a laser treatment and/or during the laser treatment and/or after the laser treatment. It is also conceivable that at least one of the one or more control parameters is repetitively, e.g., continuously, determined during the laser treatment.

The crosslinking control system may further comprise an acquisition apparatus configured to acquire information about the tissue before, during and/or after the application or introduction of the photosensitizer. The acquisition apparatus may comprise or may be configured as at least one of an Oculyzer™, an Allegro Analyzer™, an Allegro Topolyzer™, an optical biometer, an Optical Coherence Tomography (OCT) device, an optical low coherence reflectometer (OLCR), a slit lamp and an eye tracker.

The acquired information about the tissue may comprise at least one of information about the thickness of the tissue and information about the stability of the tissue. The control computer may be programmed to determine, based on the acquired information about the tissue, whether crosslinking is required. The control computer may be programmed to determine the one or more control parameters, if it is determined that crosslinking is required.

The Oculyzer™ may be based on Scheimpflug technology, providing non-contact measurement and analysis of the complete anterior eye segment. Measurements may be performed from the anterior surface of the cornea to the back of the lens. The Allegro Analyzer™ may be configured to measure the complete optics of the eye and to calculate individual wavefront aberrations. The Allegro Topolyzer™ may be configured to provide non-contact topography, keratometry, and pupilometry. The optical biometer may be configured to capture axial eye dimensions and anterior segment measurements. Measurements may include axial length, central corneal thickness, anterior chamber depth, central lens thickness, and retina thickness. Additionally, the optical biometer may provide information concerning keratometry, white-to-white distance, and pupilometry. The slit lamp may be regarded as an instrument comprising a high-intensity light source that can be focused to shine a thin sheet of light into the eye. It may be used in conjunction with a biomicroscope. The slit lamp may facilitate an examination of the anterior segment, or frontal structures and posterior segment, of the human eye, which includes the eyelid, sclera, conjunctiva, iris, natural crystalline lens, and cornea. A binocular slit lamp examination may provide a stereoscopic magnified view of the eye structures in detail, enabling anatomical diagnoses to be made for a variety of eye conditions. An eye tracker may be configured to track eye movements.

The control computer may be programmed to determine whether crosslinking is required for the respective tissue. For example, the control computer may be configured to determine a result of the crosslinking based on the information about the tissue. For example, the control computer may determine, based on the information about the tissue, whether (further) application or introduction of the photosensitizer onto or into the cornea and/or whether (further) irradiation of the photosensitizer with the light is necessary. If it is determined by the control computer that (further) crosslinking is required, the control computer may determine the one or more control parameters (again).

The crosslinking control system may further comprise an output unit to output the determined one or more control parameters. The output may in this way be considered by a treating physician. If the treating physician agrees with the (recommended) control parameters(s) as being output by the output unit, he/she can approve the output and the control computer uses the approved control parameter(s) for the control. The treating physician may also change one or more of the output (recommended) parameter(s) and the control computer may use the changed set of control parameters for control.

The crosslinking control system may be connectable to a computer network or a server to retrieve data from and/or store data in the computer network or the server.

According to a second aspect, the use of the crosslinking control system as described herein for control of crosslinking in tissue is provided.

According to a third aspect, a laser system is provided. The laser system comprises: a crosslinking control system as described herein and a laser apparatus configured to irradiate tissue with laser radiation.

According to a fourth aspect, a crosslinking control method is provided. The crosslinking control method comprises: providing photosensitizer for introduction or application of the photosensitizer into or onto tissue; providing light having a wavelength suitable to activate the photosensitizer introduced into or applied onto the tissue for crosslinking; and determining one or more control parameters for control of at least one of the activation of the photosensitizer and the introduction or application of the photosensitizer.

The crosslinking control method may further comprise: introducing or applying photosensitizer into or onto tissue in accordance with the determined one or more control parameters.

Alternatively or additionally, the crosslinking control method may further comprise: irradiating the photosensitizer introduced into or applied onto the tissue with the light in accordance with the determined one or more control parameters.

According to a fifth aspect, a method for laser treatment is provided. The method for laser treatment comprises: providing laser radiation; irradiating tissue with the laser radiation to perform laser treatment; and performing the crosslinking control method, as described herein, before, during and/or after the laser treatment.

DETAILED DESCRIPTION

Figure 2:
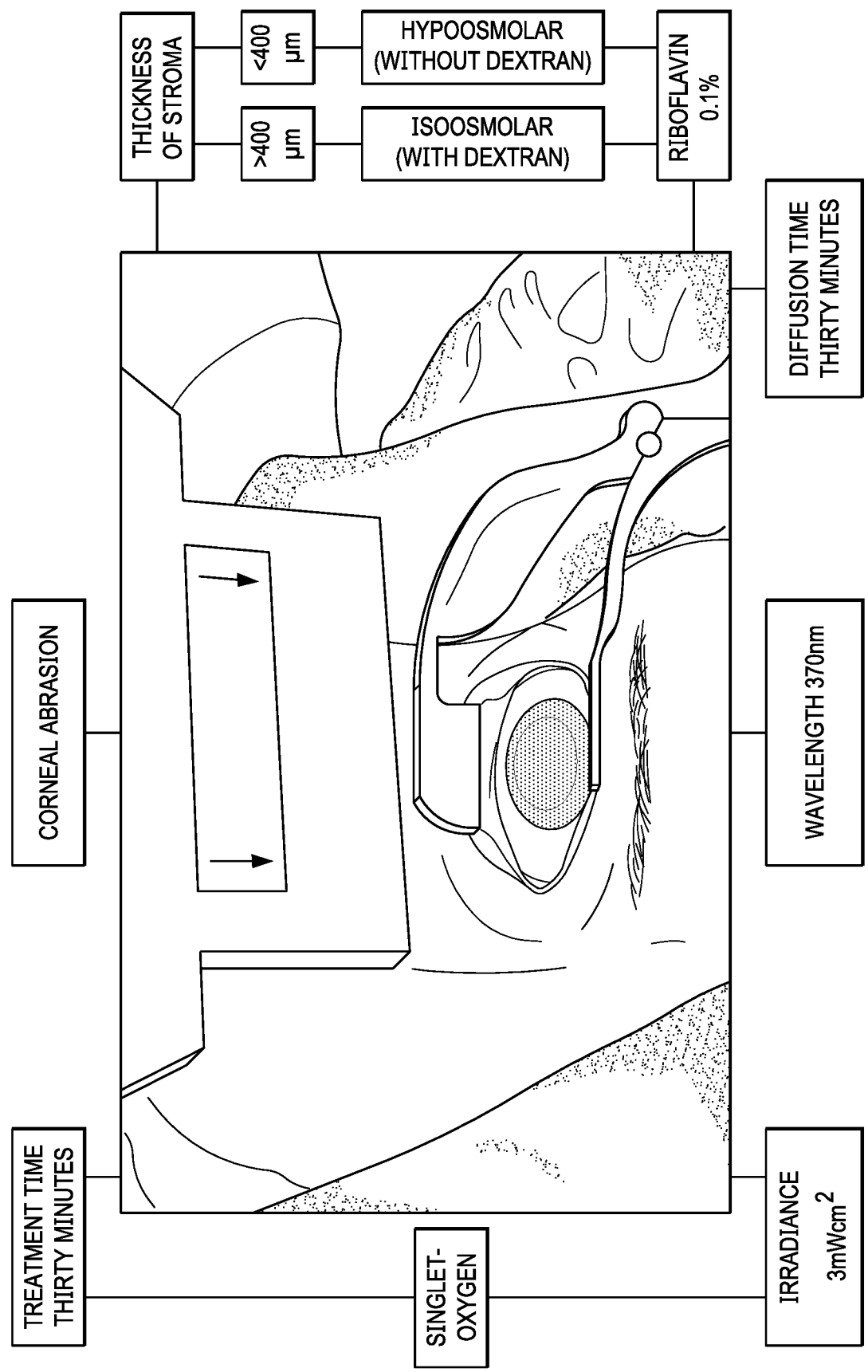
Figure 3:
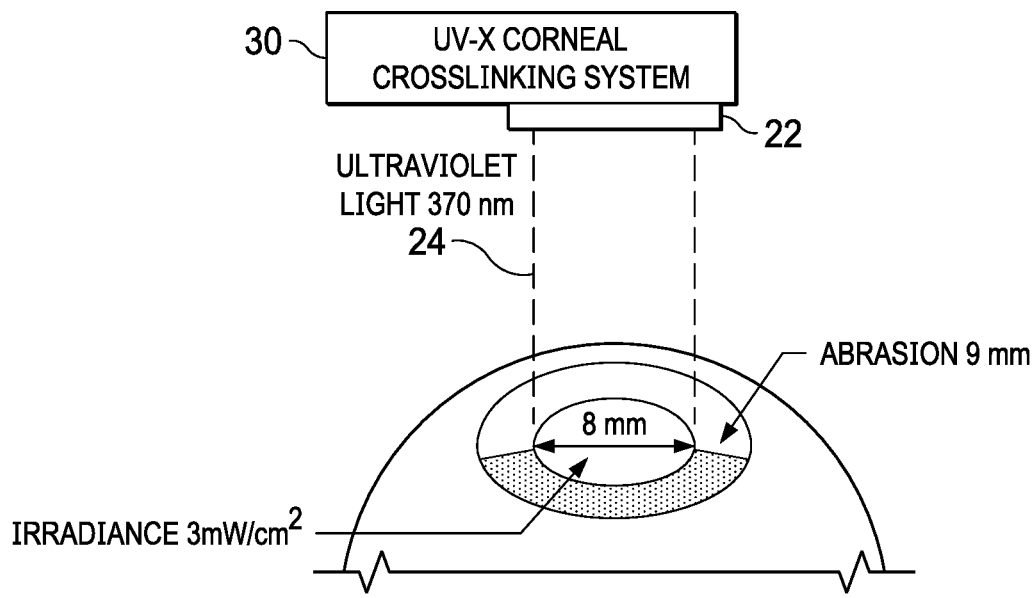
Figure 4:
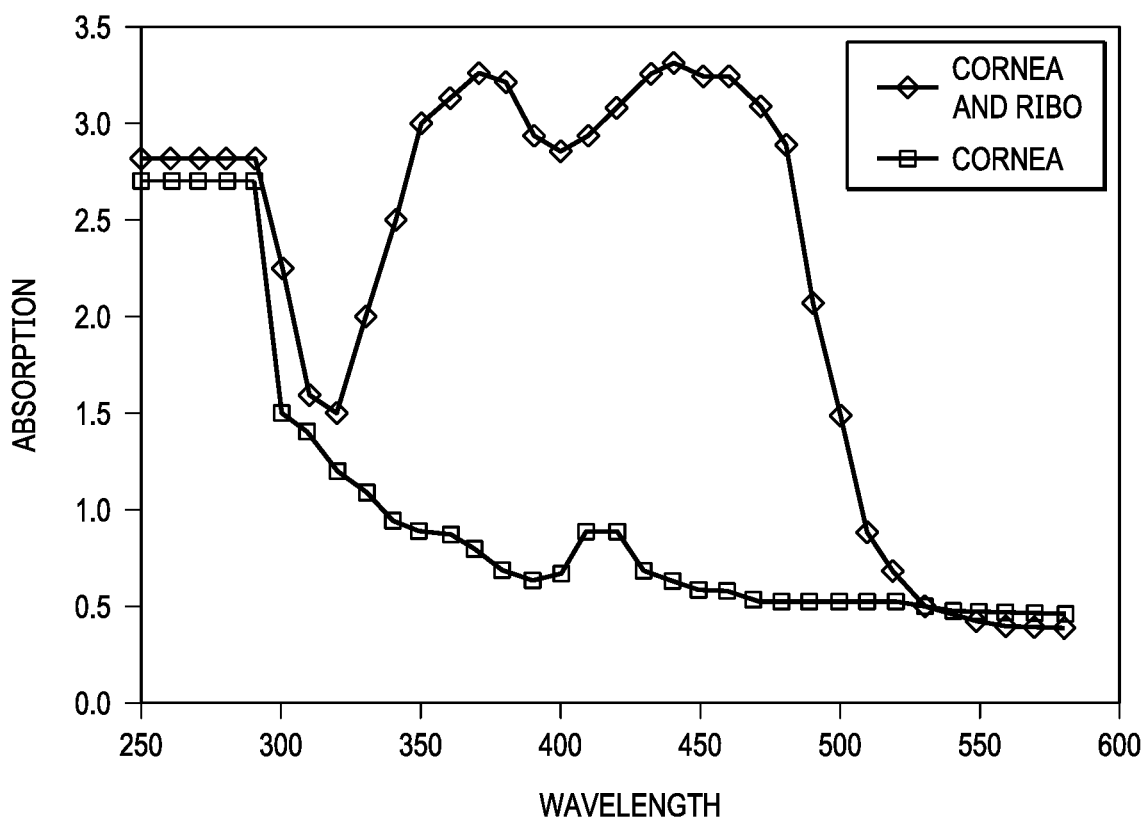
Figure 5:
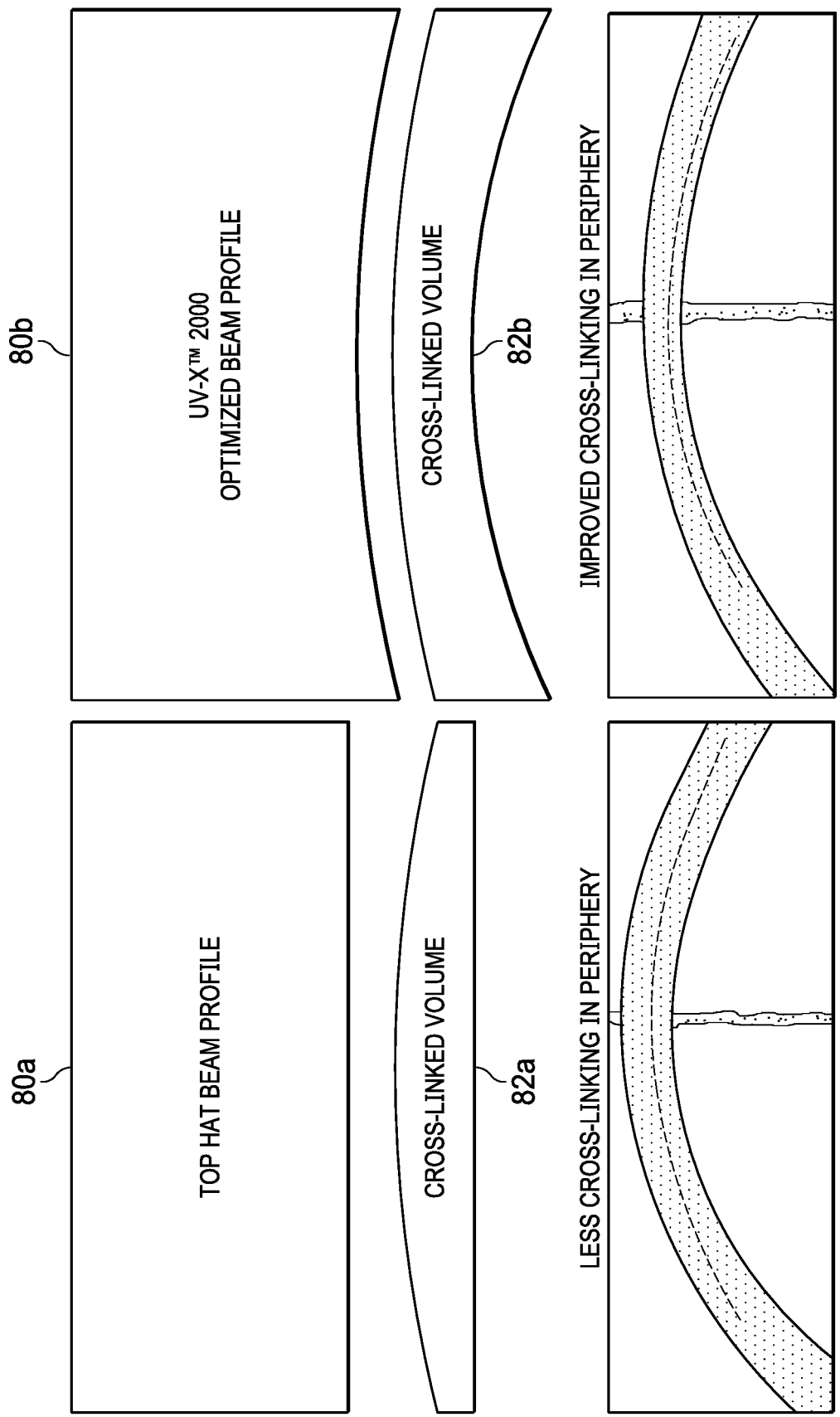
Figure 6:
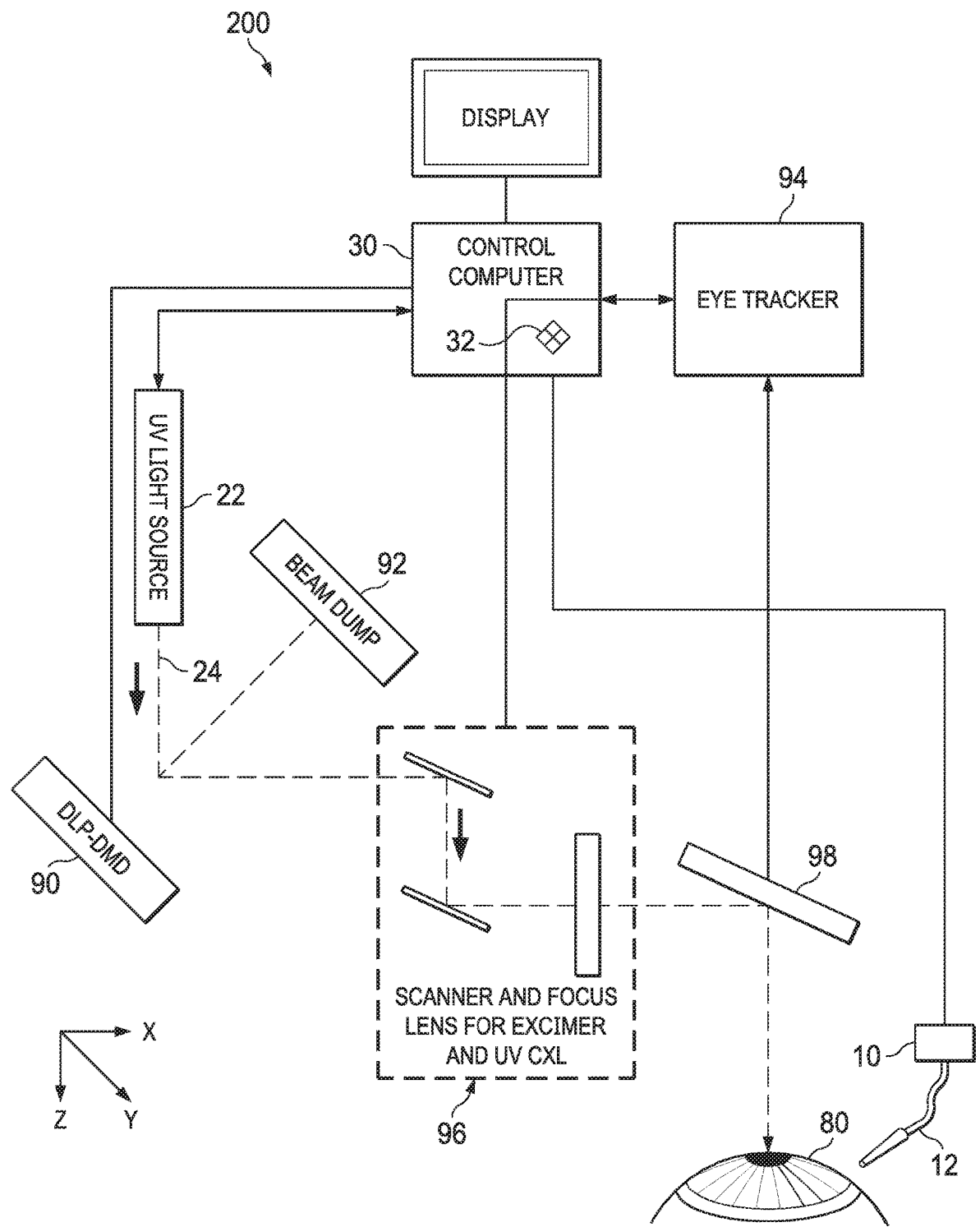
Figure 7A:
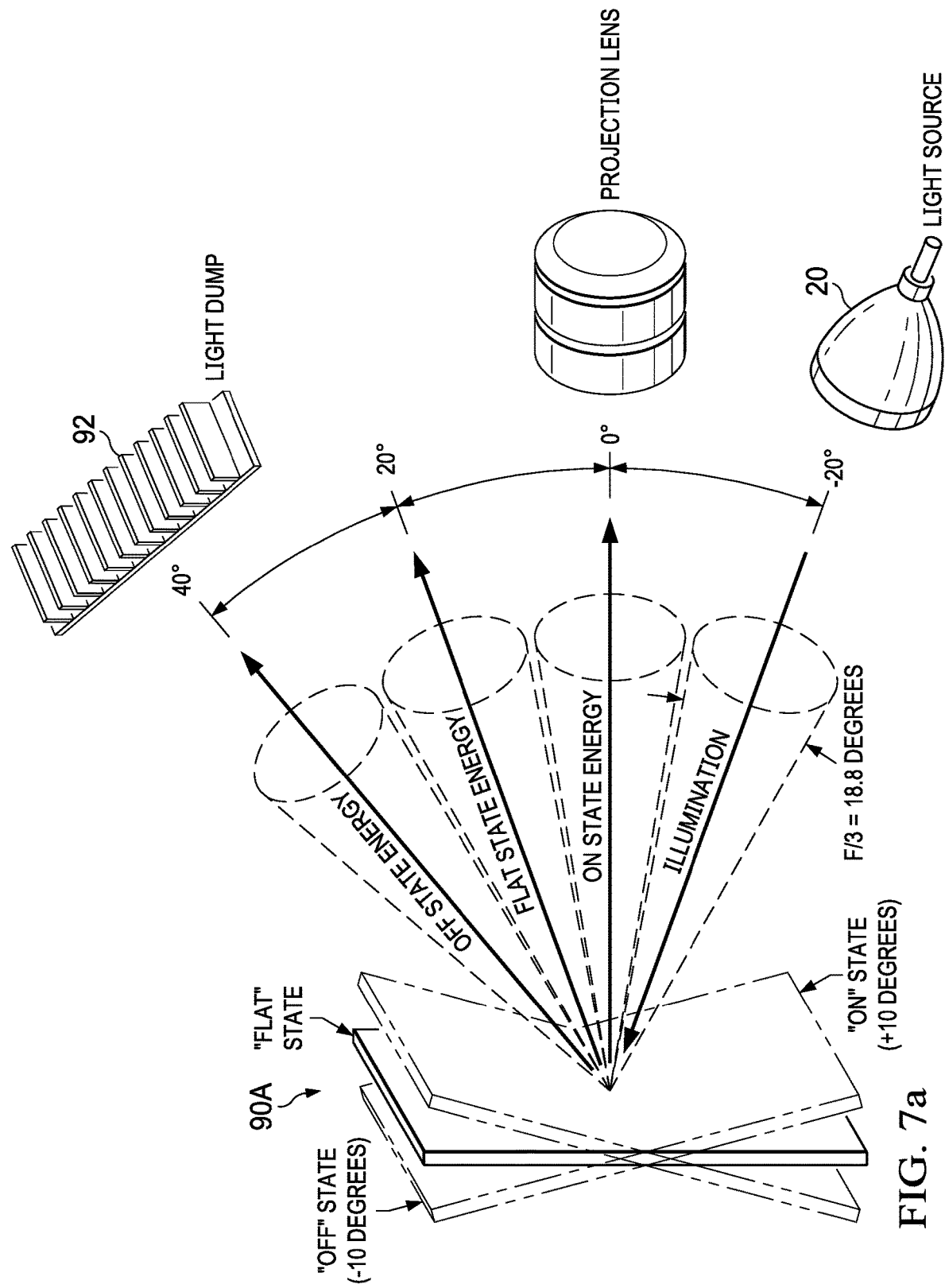
Figure 7B:
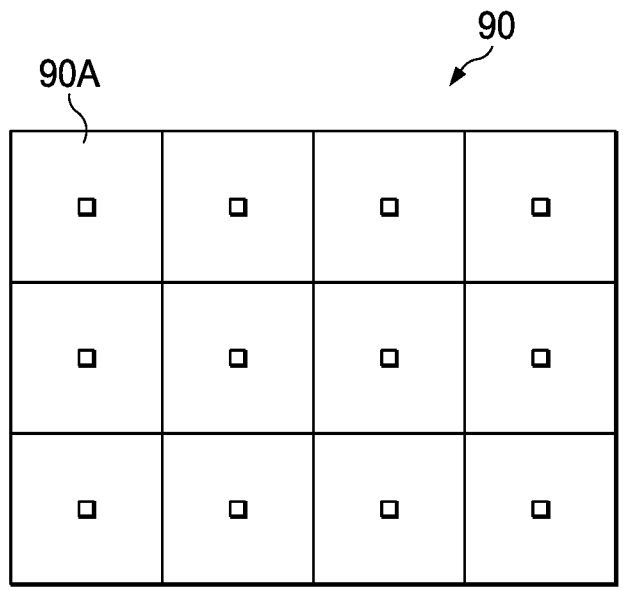
Figure 8:
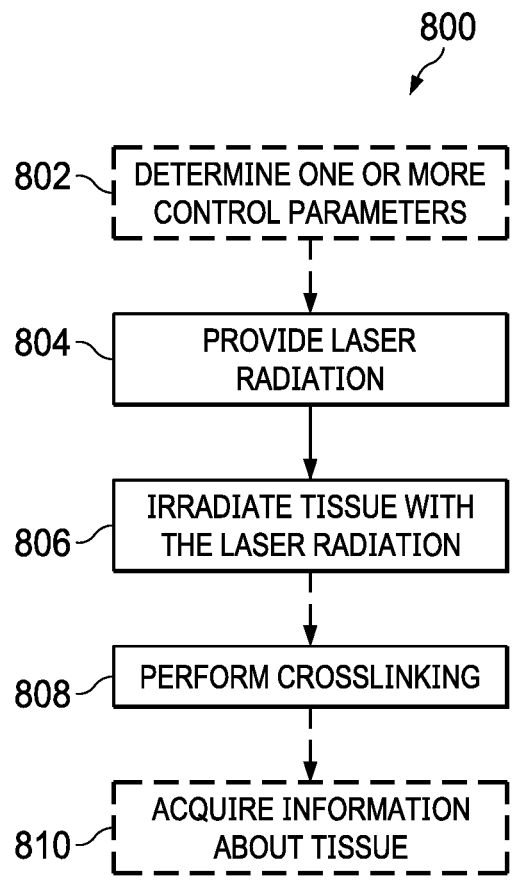
Figure 9A:
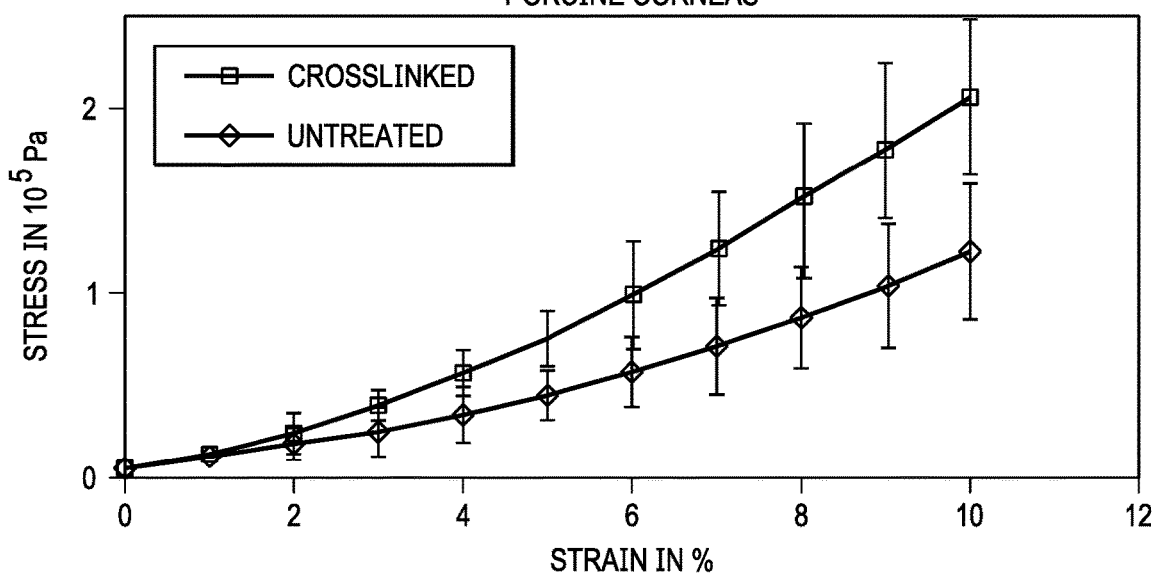
Figure 9B:
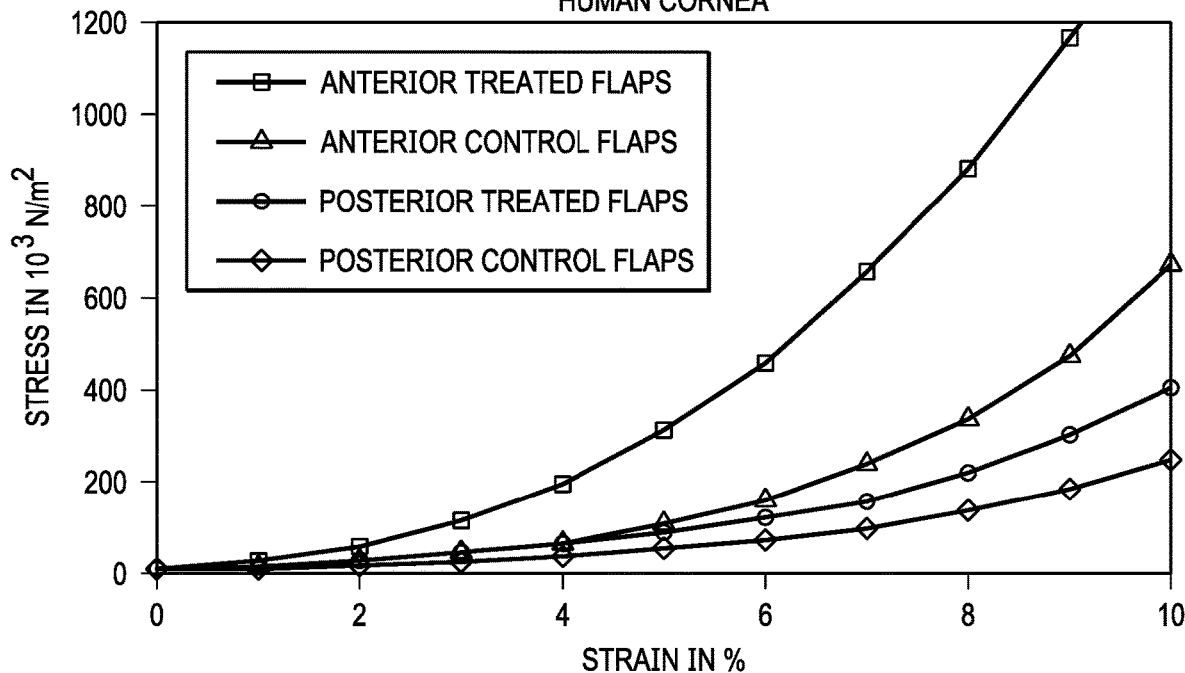

Embodiments of the present disclosure will now be described by way of example in greater detail with reference to the attached drawings, in which:

FIG. 1 schematically illustrates an example of a laser system comprising a crosslinking control system according to a first embodiment;

FIG. 2 schematically illustrates control parameters recommended by the crosslinking control system of FIG. 1;

FIG. 3 schematically illustrates irradiation by means of the crosslinking control system according to the first embodiment of FIG. 1;

FIG. 4 schematically illustrates the absorption characteristics of a human cornea over wavelength;

FIG. 5 schematically illustrates two examples for a light adjustment apparatus;

FIG. 6 schematically illustrates an example of a laser system comprising a crosslinking control system according to a second embodiment;

FIGS. 7a and 7b schematically illustrate the concept of a light adjustment apparatus used in the crosslinking control system of FIG. 6;

FIG. 8 schematically illustrates a flowchart of a method for laser treatment; and FIGS. 9a and 9b schematically illustrate the stress of the human cornea with and without corneal crosslinking.

Referring now to the drawings, example embodiments of the disclosed systems and methods are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example of a laser system 100 comprising a crosslinking control system according to a first embodiment. The crosslinking control system comprises a photosensitizer providing unit 10 which in the following will be referred to as riboflavin dispensing unit 10 because, in the present example for sake of explanation rather than limitation, riboflavin is used by way of example as a photosensitizer and the photosensitizer providing unit 10 is not only configured to provide photosensitizer but also to dispense the photosensitizer. The laser system 100 further comprises a guiding device 12. The guiding device 12 may be part of the riboflavin dispensing unit 10 or may be a separate unit. The guiding device 12 is configured to guide the riboflavin provided by the riboflavin dispensing unit 10 at intended locations as will be described in more detail below. Further, the crosslinking control system comprises a light source 20. In the present example, the light source comprises, by way of example, an UV light source 22 configured to provide light 24 in the UV spectrum, which is sometimes in the following also referred to as UV light 24. Further, by way of example, the light source 20 comprises a slit lamp 26 providing high-intensity light 28 as an example of a part of an acquisition apparatus. However, it is equally possible that the light source 20 does not comprise any acquisition apparatus or comprises different components in the acquisition apparatus than the slit lamp 26, i.e., the slit lamp 26 is optional only. For example, the light source 20 may comprise only the UV lamp 22. It is also conceivable that the acquisition apparatus, e.g., comprising the slit lamp 26, is arranged somewhere else than as a part of the light source 20.

The slit lamp 26 provides high-intensity light 28 to facilitate an examination of the anterior segment, or frontal structures and posterior segment, of the eye the patient 60.

Still further, in the present example, the crosslinking control system comprises a control computer 30. In the example shown in FIG. 1, the control computer 30 comprises separate control units, namely a riboflavin control unit 32, a lamp control unit 34 and a laser control unit 36. The riboflavin control unit 32 is configured to control the riboflavin dispensing unit 10 and/or the guiding device 12. The lamp control unit 34 is configured to control the light source 20. For example, the lamp control unit 24 may be configured to control the UV light source 22 and the slit lamp 26 independently from each other. The laser control unit 36 is configured to control a laser source 50 providing excimer laser radiation or ultrashort-pulsed laser radiation. Ultrashort may be regarded as specifying pulse duration within the nanosecond, picosecond or femtosecond or attosecond range. Unlike the example shown in FIG. 1, the riboflavin control unit 32, the lamp control unit 34 and the laser control unit 36 may also be contained in the control computer 30 as one single control unit rather than as separate control units.

Likewise, the control computer may only comprise one or more of the riboflavin control unit 32 and the lamp control unit 34. In this case, the laser control unit 36 may be arranged independently from the control computer 30 in the laser system 100. Information acquired by an additional camera system may be considered in the control computer in order to control one or more of the components of the laser system 100.

Although the UV light source 22 and the laser source 50 are shown as separate units for providing radiation with different characteristics, it is also conceivable that only one radiation source is provided, which is configured to provide suitable radiation. The radiation may then be controlled such that it is suitable for both creating, in tissue, at least one incision for the introduction or application of photosensitizer into or onto the tissue, and activating the photosensitizer for corneal crosslinking. The foregoing is described in unpublished application PCT/EP2013/051574 of the applicant, which is hereby incorporated by reference.

Independent of the exact realization of the control computer 30, the riboflavin control unit 32 is configured to control at least one of the riboflavin dispensing unit 10 and the guiding device 12, the lamp control unit 34 is configured to control the light source 20, and the laser control unit 36 is configured to control the laser source 50, e.g., an excimer or femtosecond laser, as will be described in more detail below.

As further shown by of example in FIG. 1, the control computer 30 is connected to a separate computer network, which is herein referred to as WaveNet™ 40. The connection may be a wireless or wired data connection. The latter is shown in FIG. 1 by way of example. WaveNet™ provides access to patient data as well as treatment and diagnostic parameters. For example, an interface is provided to allow access to practice-specific electronic medical records upon request. After (re)connecting to the WaveNet™ network, treatment parameters can be transferred to and from the laser system 100. Still further, as shown in FIG. 1, the patient 60 to be treated is arranged on a bedchair or patient bed 70 of the laser system 100.

The control computer 30 is configured to determine one or more control parameters for control of one or more of the components of the crosslinking control system and/or the laser system 100. With respect to FIG. 1, the control computer 30 is, by way of example, configured to control the riboflavin dispensing unit 10 (by means of the riboflavin control unit 32), to control the guiding device 12, to control the light source 20 (by means of the lamp control unit 34), and to control the laser source 50 (by means of the laser control unit 36). The control computer 30 may consider the information of the patient's eye illuminated by the slit lamp 26 and acquired by further components, e.g., a camera system, in order to determine the one or more control parameters.

Some exemplary control parameters are shown in FIG. 2 with respect to an ongoing laser surgical treatment of an eye. For illustration rather than limitation the control parameters of FIG. 2 are determined with reference to treatment of corneal abrasion as one example of laser surgical treatment. Corneal abrasion is a medical condition involving the loss of the surface epithelial layer of the eye's cornea.

As shown in FIG. 2, the control computer 30 is configured to determine the photosensitizer to be used. For this purpose, the control computer 30 may instruct an acquisition apparatus to acquire information about the pre-operative thickness of the cornea. If the pre-operative thickness of the cornea is smaller than 400 μm, the control computer 30 may recommend hypoosmolar riboflavin. If, however, the preoperative thickness of the cornea is larger than 400 µm, the control computer 30 may recommend isoosmolar riboflavin.

Further, in the example of FIG. 2, the control computer 30 computes a concentration of riboflavin to be introduced into or applied onto the cornea. For example, the control computer 30 recommends a concentration of 0.1%. The control computer 30 further computes a recommended diffusion time indicating how long riboflavin shall be introduced into or applied onto the cornea. In the example shown in FIG. 2, the control computer 30 exemplarily computes a diffusion time of 30 minutes. In order to determine a recommended concentration and diffusion time, the control computer 30 may consider information about the thickness of the cornea (or other information about the eye tissue) and information about the recommended photosensitizer.

Still further, depending on the type and/or concentration of the recommended photosensitizer, the control computer 30 computes a recommended wavelength of UV light for irradiation of the recommended photosensitizer. For this purpose, for each conceivable photosensitizer, type of photosensitizer, and/or concentration of the photosensitizer, absorption characteristics over the wavelength may be stored in the control computer 30 or in the WaveNet™ 40. These absorption characteristics may then be retrieved by the control computer 30 in order to determine a wavelength suitable to activate the recommended photosensitizer. One example for such absorption characteristics is shown in FIG. 4 for riboflavin. As can be seen therefrom, riboflavin has an absorption maximum at 370 nm. In consequence, if riboflavin is used as the photosensitizer, the control computer may recommend a wavelength of 370 nm for irradiation of the riboflavin.

As further shown in FIG. 2, the control computer 30 calculates a recommended intensity of light 24 for irradiation of the riboflavin, which is called irradiance in FIG. 2. For example, 3 mW/cm$^2$ may be recommended by the control computer 30. The control computer 30 may determine the irradiance by considering information about the thickness of the cornea (or other information about the eye tissue), information about the recommended photosensitizer and information about the recommended wavelength.

Still further, the control computer 30 computes a recommended treatment time indicating how long the introduced or applied riboflavin is to be irradiated with the light 24. In the example shown in FIG. 2, the control computer 30 exemplarily computes a treatment time of 30 minutes. In order to determine the recommended treatment time, the control computer 30 may consider information about the thickness of the cornea (or other information about the eye tissue), information about the recommended photosensitizer and/or information about the recommended wavelength and irradiance of the light 24. The control parameters shown in FIG. 2 are purely exemplary and different or further control parameters may be determined and recommended by the control computer 30.

After determining the exemplary control parameters as given in FIG. 2 and as explained above with reference to FIG. 2, the control computer 30 outputs the determined control parameters as a recommendation on an output unit, e.g., a display or the like. The treating physician may approve the recommended control parameters or may change one or more of the recommended control parameters, for example, by means of a touch input on the display. If one or more of the control parameters are changed by the treating physician, the control computer may adjust at least some of the other control parameters by considering the changes input by the treating physician. Once all control parameters are set, the control computer controls the riboflavin dispensing unit 10, the guiding device 12 and the light source 20 in accordance with the set control parameters.

For example, the control computer 30 may instruct the riboflavin dispensing unit 10 to dispense hypoosmolar riboflavin with a concentration of 0.1% and a diffusion time of 30 minutes. The control computer 30 may instruct the guiding device 12 to guide the riboflavin as dispensed by the riboflavin dispensing unit 10 to specific locations into or onto the cornea. Further, the control computer 30 may instruct the UV light source 22 of the light source to provide light with a wavelength of 370 nm and an irradiance of 3 mW/cm$^2$ on the tissue to be irradiated during a treatment time of 30 minutes.

FIG. 3 shows how some of the exemplary treatment parameters are used for irradiation. For example, the control computer 30 instructs the UV light source 22 to irradiate a circle-shaped area (crosslinking area) with a diameter of 8 mm. Further, the control computer 30 instructs the UV light source 22 to provide UV light 24 having a wavelength of 370 nm. The control computer 30 further instructs the UV light source 22 to generate UV light 24 with an irradiance of 3 mW/cm$^2$ on the crosslinking area to be irradiated.

In order to achieve a homogeneous illumination over the desired crosslinking area of FIG. 3 having a diameter of about 8 mm, different intensity profiles (spatial distributions) may be used for the light. For example, a top hat shaped profile 80a as shown on the left side of FIG. 5 can be used or a donut like distribution 80b as shown on the right side of FIG. 5 can be used. In dependence of the intensity profile used, different areas or volumes within the eye can be irradiated to create different crosslinked volumes within the eye.

FIG. 6 shows another example of a laser system 200 comprising a crosslinking control system according to a second embodiment. The crosslinking control system according to the second embodiment basically corresponds to the crosslinking control system according to the first embodiment. Unlike the first embodiment, the crosslinking control system according to the second embodiment does not comprise a slit lamp 26 (cf. FIG. 1). However, an UV light source 22 is also provided in the second embodiment. Further, the crosslinking control system of the second embodiment has one single control computer 30 and additionally comprises a Digital Light Processing (DLP)-DMD device 90 and an eye tracker 94. By means of the eye tracker 94, movements of the eye, for example, during surgery may be determined and corresponding data may be forwarded to the control computer 30 for consideration. In other words, eye movements during surgery may be compensated by the use of the eye tracker to follow the eye movement. For this purpose, the control computer may consider the eye movement data for determining the one or more control parameters. If eye movement is not considered, the eye movement may interfere with the intended crosslinking area, which may result in the crosslinking area being larger and non-symmetric due to the eye movements. However, if the eye movements are followed and considered by the control computer 30, exact application of the UV light 24 can be achieved.

For example, the control computer 30 may consider the eye movement data to determine the spatial distribution of the light 24. For example, the control computer 30 may slightly adjust the spatial distribution of the light 24 based on the movement of the eye 80. In this way, at least almost the same crosslinking area can be irradiated despite the movements of the eye 80. The eye tracker may follow translation movements of the eye in the x-y-z direction, rotational movements of the eye in the x-y-direction as well as eye torsion, i.e., cyclotrosion.

The DLP-DMD device 90 serves as another example of a light adjustment apparatus. The DMD concept is briefly explained with respect to FIGS. 7a and 7b. As shown in FIG. 7a, light provided by a light source 20 and incident on one DMD element 90a, is reflected in dependence of the state of the DMD element 90a. Each DMD element is typically formed by a mirror. For example, depending on the tilt angle of the DMD element 90a, the light can be reflected on a light dump 92. The foregoing may also be referred to as the off state of the DMD element 90a. Alternatively, depending on the tilt angle of the DMD element 90a, the light can be reflected on a projection lens. The foregoing may also be referred to as the on state of the DMD element 90a. As can be further seen in FIG. 7b, a typical DMD device normally comprises a plurality, e.g., several hundred or several thousand, of DMD elements 90a. For example, the DLP-DMD device 90 may comprise 1000×1000 or even more DMD elements 90a. The DLP-DMD device 90 (DLP-DMD chip 90) may comprise even up to millions of DMD elements 90a configured as tiny, microscopic mirrors which reflect light digitally. Each of these DMD elements 90a of one DLP-DMD device 90 (which may also be referred to as DLP-DMD chip 90) can be controlled and tilted independently from each other. For example, each individual DMD element 90a can be switched on (into its on state) or off (into its off state) by applying a voltage to an address electrode of the DMD element 90a.

When using such a DLP-DMD device 90 in the cross-linking control system, the spatial distribution of the UV light 24 can be precisely controlled by means of the DLP-DMD device 90 according to the instructions received from the control computer 30. In other words, the DLP-DMD device 90 may act as a light shaping device for individually shaping the UV light 24 to any desired pattern or shape. For example, the control computer 30 can instruct each of the DMD elements 90a of the DLP-DMD device 90 to move to a specific tilt angle, in order to irradiate the eye 80 with the intended spatial distribution as computed by the control computer 30 or as input by a treating physician. In order to determine the tilt angles of the DMD elements 90a, the control computer 30 may consider the eye movement data acquired by the eye tracker 94. The control computer 30 may then instruct the UV light source 22 and the DLP-DMD device 90 accordingly. For example, the control computer 30 may instruct the UV light source 22 and the DLP-DMD device 90 to shape the intensity profile and the spatial distribution in the desired manner. Further, the control computer 30 may instruct an x-y scanner to move the UV light 24 in accordance with the eye movements.

Summarizing the above, the control computer 30 determines one or more control parameters, e.g., the control as shown in FIG. 2. The control computer 30 instructs the UV light source 22 to irradiate UV light 24 in accordance with the determined control parameters, for example, UV light having a wavelength of 370 nm and an irradiance on the patient's eye of 3 mW/cm². The control computer 30 also determines a recommended spatial distribution and, when the spatial distribution is approved by the treating physician, instructs the DMD elements 90a of the DLP-DMD device 90 to assume certain tilt angles respectively. The UV light 24 is guided to the DLP-DMD device 90 and is partially either reflected on the beam dump 92 or via an x-y scanner and beam combiner 98 on the patient's eye 80. The x-y scanner 96 is used to compensate the movement of the patient's eye 80, which was detected by eye tracker 94 and controlled by the control computer 30. By partially reflecting some of the UV light 24 on the beam dump 92, while guiding some of the UV light 24 to the patient's eye 80, partial areas of the patient's eye 80 can be selectively irradiated or not depending on the state of the DMD elements 90a. The control computer 30 may further determine a treatment time of 30 minutes. During this treatment time, the patient's eye 80 is irradiated with the UV light 24. Further, during the treatment time, the eye tracker 94 repetitively, e.g., continuously, tracks the movement of the patient's eye 80 and forwards the acquired movement data to the control computer 30. The control computer 30 can then adjust one or more of the control parameters on the basis of the movement data. For example, the control computer may instruct at least some of the DMD elements 90a to change their tilt angles. In this way, the UV light 24 may irradiate the patient's eye with the intended spatial distribution despite of the eye movement. By means of the DMD device 90, an individual beam shape profile of the UV light 24 may be formed. This may facilitate activating the photosensitizer locally at certain points or areas. In this way, the eye tissue can be precisely hardened in the way desired by the treating physician or required by the laser treatment to be or already being performed.

The hardened cornea may then be treated with laser radiation provided by a laser source (not shown but part of component arrangement 96). The component arrangement 96 may further comprise the x-y scanner and a focus lens to guide and focus the laser radiation. The laser radiation can then irradiate the eye 80 to perform any conceivable laser treatment of the eye like LASIK, IntraLASIK, photorefractive keratectomy (PRK, LASEK), laser thermal keratoplasty or phototherapeutic keratectomy (PTK).

A method embodiment for laser treatment 800 is shown in the flowchart of FIG. 8. In a first optional step 802, one or more control parameters may be determined by the control computer 30, as described herein, before laser treatment is performed. Then, laser radiation is provided by a laser source (step 804) and the eye tissue is irradiated with the laser radiation to perform laser treatment (step 806). During the laser treatment, one or more control parameters may be determined or adjusted by the control computer 30, as described herein.

Then riboflavin may be introduced into the cornea or applied onto the cornea and the eye tissue may be irradiated with the UV light in accordance with the one or more determined or adjusted control parameters (step 808) to perform crosslinking. The steps 802 and 808 may be regarded as steps of a crosslinking control method.

Finally, information about the tissue may be acquired by an acquisition apparatus in a further optional step 810 before, during and/or after the treatment. By means of the information about the tissue acquired after the treatment, the control computer 30 may determine whether the treatment was successful. The step 810 may also be a step of the crosslinking control method.

As can be seen from FIG. 9a, corneal crosslinking increases drastically the stress on the corneal tissue. The best results are achieved by means of anterior treated flaps (see FIG. 9b).

The invention claimed is:
1. A crosslinking control system comprising:
a photosensitizer dispensing unit configured to dispense photosensitizer for introduction or application of the photosensitizer into or onto tissue;

a light source configured to provide light having a wavelength suitable to activate the photosensitizer introduced into or applied onto the tissue for crosslinking;

a light adjustment apparatus comprising a Digital Light Processing-Digital Micromirror Device (DLP-DMD) configured to adjust the spatial distribution of the light;

an acquisition apparatus configured to acquire information about the tissue at least before the application or introduction of the photosensitizer, the information including information about the thickness of the tissue; and a control computer programmed to:
  determine a type of photosensitizer to be used according to the thickness of the tissue: if the thickness is greater than a predetermined thickness of 400 μm, a first type of photosensitizer is to be used, if the thickness is less than the predetermined thickness of 400 μm, a second type of photosensitizer different from the first type is to be used;
  determine one or more control parameters for control of at least one of the activation of the photosensitizer and the introduction or application of the photosensitizer, the one or more control parameters for control of the activation of the photosensitizer including: information specifying the spatial distribution of the light in or on the tissue and information specifying the determined type of photosensitizer;
  control the photosensitizer dispensing unit to provide the determined type of photosensitizer;
  control the light adjustment apparatus to adjust the spatial distribution of the light in or on the tissue; and
  wherein the tissue is a cornea, the first type of photosensitizer is isoosmolar riboflavin and the second type of photosensitizer is hypoosmolar riboflavin.

2. The crosslinking control system of claim 1, wherein the one or more control parameters for control of the activation of the photosensitizer further or additionally comprise at least one of information specifying the duration of irradiation of the photosensitizer with the light, information specifying the intensity of the light for irradiating the photosensitizer, information specifying the wavelength of the light for irradiating the photosensitizer, and information specifying the temporal distribution of the light in or on the tissue.

3. The crosslinking control system of claim 1, wherein the one or more control parameters for control of the introduction or application of the photosensitizer further or additionally comprise at least one of information specifying the quantity of the photosensitizer to be introduced or applied into or onto the tissue, information specifying one or more positions in or on the tissue for the introduction or application of the photosensitizer, and information specifying one or more points or periods of time for the introduction or application of the photosensitizer.

4. The crosslinking control system of claim 1, wherein the control computer is programmed to control at least one of the activation of the photosensitizer and the introduction or application of the photosensitizer by considering the determined one or more control parameters.

5. The crosslinking control system of claim 1, wherein the control computer is programmed to control the photosensitizer dispensing unit to provide the photosensitizer for the introduction or application of the photosensitizer in accordance with the determined one or more control parameters.

6. The crosslinking control system of claim 1, wherein the control computer is programmed to control the light adjustment apparatus to further or additionally change at least one of the duration of irradiation of the photosensitizer with the light, the intensity of the light for irradiating the photosensitizer, the wavelength of the light for irradiating the photosensitizer, and the temporal distribution of the light in or on the tissue in accordance with the determined one or more control parameters.

7. The crosslinking control system of claim 6, wherein the light adjustment apparatus further or additionally comprises at least one member of a set consisting of a diaphragm and a beam delimiter.

8. The crosslinking control system of claim 1, wherein the control computer is configured to repetitively determine the one or more control parameters.

9. The crosslinking control system of claim 1, wherein the photosensitizer dispensing unit further comprises a guiding device configured to guide the photosensitizer into or onto the tissue in accordance with the determined one or more control parameters.

10. The crosslinking control system of claim 1, wherein the acquisition apparatus is configured to further or additionally acquire information about the tissue at least during or after the application or introduction of the photosensitizer.

11. The crosslinking control system of claim 10, wherein the control computer is programmed to determine a result of the crosslinking based on the information about the tissue.

12. The crosslinking control system of claim 10, wherein the crosslinking control system further comprises a display to output the determined one or more control parameters.

13. The crosslinking control system of claim 1, wherein the acquisition apparatus comprises at least one member of a set consisting of an oculyzer, an analyzer, a topolyzer, an optical biometer, an optical coherence tomography device, and an eyetracker.

14. The crosslinking control system of claim 1, wherein the acquired information about the tissue further or additionally comprises information about the stability of the tissue.

15. The crosslinking control system of claim 1, wherein the control computer is programmed to:
  determine, based on the acquired information about the tissue, whether crosslinking is required, and
  if it is determined that crosslinking is required, to determine the one or more control parameters.

16. The crosslinking control system of claim 1, wherein the light source comprises or is configured as at least one member of a set consisting of an ultraviolet, UV, light source, UV light emitting diode, LED, glass fiber, and light waveguide.

17. The crosslinking control system of claim 1, wherein the crosslinking control system is connectable to a computer network or a server to retrieve data from and/or store data in the computer network or the server.

18. The crosslinking control system of claim 1, wherein the control computer is programmed to control the light adjustment apparatus to adjust the spatial distribution of the light in or on the tissue to have a donut-like distribution to yield improved cross-linking in the periphery of the tissue.

* * * * *